United States Patent
Brown

(10) Patent No.: US 6,907,889 B2
(45) Date of Patent: *Jun. 21, 2005

(54) NON-CRYSTALLINE SALIVA-SOLUBLE COATINGS FOR ELASTOMERIC MONOFILAMENT DENTAL TAPES

(75) Inventor: Dale G. Brown, Wharton, TX (US)

(73) Assignee: International Tape Partners, LLC, Stafford, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/613,692

(22) Filed: Jul. 3, 2003

(65) Prior Publication Data

US 2004/0094181 A1 May 20, 2004

Related U.S. Application Data

(63) Continuation of application No. 09/935,921, filed on Aug. 23, 2001, now Pat. No. 6,609,527.
(60) Provisional application No. 60/263,220, filed on Jan. 22, 2001.

(51) Int. Cl.$^7$ .................................................. A61K 7/16
(52) U.S. Cl. ............................................ 132/321; 424/49
(58) Field of Search ................................. 132/321, 200; 424/49, 50, 401, 443; 433/216

(56) References Cited

U.S. PATENT DOCUMENTS

| | | | |
|---|---|---|---|
| 3,664,915 A | 5/1972 | Gore | 161/164 |
| 3,800,812 A | 4/1974 | Jaffe | 132/89 |
| 3,953,566 A | 4/1976 | Gore | 364/288 |
| 3,962,153 A | 6/1976 | Gore | 260/2.5 R |
| 4,096,227 A | 6/1978 | Gore | 264/210 R |
| 4,187,390 A | 2/1980 | Gore | 174/102 R |
| 4,256,806 A | 3/1981 | Snyder | 428/378 |
| 4,385,093 A | 5/1983 | Hubis | 428/316.6 |
| 4,478,665 A | 10/1984 | Hubis | 156/229 |
| 4,776,358 A | 10/1988 | Lorch | 132/321 |
| 4,911,927 A | 3/1990 | Hill et al. | 424/443 |
| 4,974,615 A | 12/1990 | Doundoulakis | 132/321 |
| 4,986,288 A | 1/1991 | Kent et al. | 132/321 |
| 5,033,488 A | 7/1991 | Curtis et al. | 132/321 |
| 5,165,913 A | 11/1992 | Hill et al. | 424/49 |
| 5,209,251 A | 5/1993 | Curtis et al. | 132/321 |
| 5,220,932 A | 6/1993 | Blass | 132/321 |
| 5,357,990 A | 10/1994 | Suhonen et al. | 132/321 |
| 5,433,226 A | 7/1995 | Burch | 132/321 |
| 5,479,952 A | 1/1996 | Zachariades et al. | 132/321 |
| 5,503,842 A | 4/1996 | Fazan et al. | 260/621 |
| 5,518,012 A | 5/1996 | Dolan et al. | 132/321 |
| 5,718,251 A | 2/1998 | Gray et al. | 132/321 |
| 5,755,243 A | 5/1998 | Roberts et al. | 132/321 |
| 5,760,117 A | 6/1998 | Chen | 524/270 |
| 5,765,576 A | 6/1998 | Dolan et al. | 132/321 |
| 5,787,758 A | 8/1998 | Sheldon | 74/490 |
| 5,845,652 A | 12/1998 | Tseng et al. | 132/200 |
| 5,848,600 A | 12/1998 | Bacino et al. | 132/321 |
| 5,875,798 A | 3/1999 | Petrus | 132/321 |
| 5,884,639 A | 3/1999 | Chen | 132/321 |
| 5,911,228 A | 6/1999 | Curtis et al. | 132/321 |
| 5,918,609 A | 7/1999 | Tsao et al. | 132/321 |
| 5,962,572 A | 10/1999 | Chen | 524/474 |
| 5,998,431 A | 12/1999 | Tseng et al. | 514/300 |
| 6,003,525 A | 12/1999 | Katz | 132/321 |
| 6,027,592 A | 2/2000 | Tseng et al. | 156/167 |
| 6,080,481 A | 6/2000 | Ochs et al. | 428/372 |
| 6,083,208 A | 7/2000 | Modak et al. | 604/265 |
| 6,148,830 A | 11/2000 | Chen | 132/321 |
| 6,161,555 A | 12/2000 | Chen | 132/321 |

*Primary Examiner*—Todd E. Manahan

(57) ABSTRACT

An improved dental tape treated with a substantive coating containing a crystal control substance, wherein said coating is: saliva soluble, substantially crystal-free, with a flaking value of less than about 20 and a release value of about 100.

32 Claims, No Drawings

NON-CRYSTALLINE SALIVA-SOLUBLE COATINGS FOR ELASTOMERIC MONOFILAMENT DENTAL TAPES

CROSS-REFERENCE TO RELATED APPLICATIONS

This application is a continuation of application Ser. No. 09/935,921, filed 23 Aug. 2001, now U.S. Pat. No. 6,609,527. That application claims priority from now abandoned U.S. Provisional Application Ser. No. 60/263,220, filed 22 Jan. 2001, the disclosure of which is hereby incorporated herein by reference.

FIELD OF THE INVENTION

The present invention relates to improved dental tapes. Specifically, the improved dental tapes of the present invention contain substantially crystal-free coatings that: (a) comprise from 20 to 120% by weight of the floss filament, (b) are saliva soluble and (c) exhibit a minimum of flaking. Yet these coatings are released in total into the oral cavity during flossing and can contain ingredients such as abrasives that work with the tape to help physically remove biofilms from interproximal and subgingival surfaces, and chemotherapeutic ingredients affecting oral health and subsequent systemic diseases caused or exacerbated by poor oral health. These coatings are particularly adapted to monofilament dental tapes.

BACKGROUND OF THE INVENTION

Historically the purpose of dental floss was: (1) to dislodge and remove decomposing food material that accumulated at interproximal and subgingival surfaces and could not be removed by brushing or rinsing, and (2) to dislodge and remove bacteria, plaque and/or calculus that accumulated since the previous flossing and/or cleaning.

The concept of the use of dental floss for cleansing interproximal spaces appears to have been introduced by Parmly in 1819. Parmly suggested the use of waxed silk to clean teeth of persons subject to gingival inflammation.

The role of plaque, now described as subgingival biofilm, in gum disease is well documented. The need to physically remove subgingival biofilms routinely has become an accepted treatment for gum disease. Mechanical removal of subgingival biofilms can be achieved professionally through: scaling, planing, prophylaxis and polishing, and individually by tooth brushing, proxy brushing and flossing.

While these methods of physically removing subgingival biofilms from tooth surfaces are effective and well accepted; gum disease continues to be prevalent in the adult population, and consequently, improved means for the individual to physically remove subgingival biofilms routinely are indicated.

Furthermore, the spacing between teeth is not uniform and it varies considerably, not only from one place to another between the same pair of teeth, but also from one pair of teeth to another pair of teeth. The spacing varies in the same individual, among different individuals, and especially in the case of twisted teeth and teeth that have fillings, crowns, etc.

To accommodate tight spacing and those interproximal contacts that do not allow multifilament dental floss to be worked between teeth without fraying, breaking, etc., a vast array of "TEFLON" dental flosses have been commercialized. These shred-resistant, monofilament tapes are described in detail in the following U.S. patents, which are hereby incorporated by reference: U.S. Pat. Nos. 3,664,915; 3,953,566; 3,962,153; 4,096,227; 4,187,390; 4,256,806; 4,385,093; 4,478,665; 4,776,358; 5,033,488; 5,209,251; 5,220,932; 5,518,012; 5,718,251; 5,765,576; and 5,911,228.

The TEFLON-type tapes available commercially in the marketplace today, include: Gore's GLIDE® dental tape, Oral-B's SATIN FLOSS® dental tape, Johnson & Johnson's EASY FLOSS® dental tape, and Colgate's TOTAL® dental tape. All of these tapes can be worked between tight spaces with a minimum of fraying and breaking. Yet, unlike their multifilament counterparts such as Johnson & Johnson's woven floss, REACH® Gentle Gum Care, during flossing, these tapes do not release substantial quantities of cleaners, abrasives, tartar control ingredients, whiteners and active ingredients such as fluoride, antimicrobials, antibiotics, etc. The net of this shortcoming in failing to deliver substantial quantities of ingredients to those sites being flossed is that the tapes are generally perceived as most convenient in fitting between teeth, but unfortunately, they are generally perceived as: "not cleaning", "not working", "not doing much", etc., once they are positioned between teeth.

When substantial quantities of cleaning, conditioning and treating substances are coated onto tapes, the resultant tapes are characterized by excessive flaking and breaking off of these coatings during processing, dispensing and wrapping of tape around the fingers. As a result, there are no commercial tapes available with substantial coatings of releasable ingredients suitable for working into and physically removing biofilms from interproximal and subgingival spaces.

Biofilms are notorious throughout nature for being difficult to remove. Working a monofilament tape over biofilms in the absence of substantial quantities of cleaners, abrasives, etc., is not effective in physically removing and/or disrupting substantial quantities of biofilms. The net is, critical biofilm buildup interproximally and subgingivally cannot be effectively physically removed with routine flossing with current commercial dental tapes, both PTFE tapes and bicomponent tapes.

Monofilament interproximal devices are described and claimed in: U.S. Pat. Nos. Re 35,439; 3,800,812; 4,974,615; 5,760,117; 5,433,226; 5,479,952; 5,503,842; 5,755,243; 5,845,652; 5,884,639; 5,918,609; 5,962,572; 5,998,431; 6,003,525; 6,083,208; 6,148,830; 6,161,555; and 6,027,592, the disclosures of which are hereby incorporated herein by reference. These dental tapes generally have serious shortcomings in gentleness, in delivering coatings during flossing and in being handled easily and conveniently during flossing Polytetrafluoroethylene (PTFE) based interproximal devices are described in: U.S. Pat. Nos. 5,209,251; 5,033,488; 5,518,012; 5,911,228; 5,220,932; 4,776,358; 5,718,251; 5,848,600; 5,787,758; and 5,765,576. To date, no commercial versions of these tapes have been coated effectively and cannot be used to deliver active ingredients, interproximally and subgingivally during flossing. Handling during flossing is difficult. Most have to provide a consumer acceptable edge. Many are plagued with serious dimensional inconsistency problems, as well.

Several Patent Applications have been filed on monofilament dental tapes with coatings comprising from between about 20% by weight and about 120% by weight of the monofilament tape. These are described in U.S. Provisional Patent Application Ser. Nos. 60/227,433 and 60/227,255, filed 23 Aug. 2000 and Ser. No. 60/263,220, filed 22 Jan. 2001, all of which are hereby incorporated by reference.

There is clearly a need for a commercial, shred-resistant tape that is coated with releasable ingredients that help disrupt and/or physically remove biofilms from critical interproximal and subgingival sites when used regularly, and deliver chemotherapeutic agents as required in a site-specific manner.

SUMMARY OF THE INVENTION

The present invention centers around the observation that the substantivity of coatings onto flexible surfaces, including dental tapes, can be enhanced such that during flexure of the surface, these enhanced coatings remain substantive to said surface and resist cracking, fracturing and flaking off. Specifically, it has been observed that most coated flexible surfaces, especially those formulated to be saliva-soluble and carry effective quantities of abrasives, cleaners, surfactants, and chemotherapeutic agents, fracture along crystal faces during flexure, thereafter releasing the ingredients from the flexible surface by cracking, chipping, flaking and/or falling off etc. In response to these observations, it has been unexpectedly found that the addition of certain substances to various coatings at relatively modest levels reduces crystal formation while simultaneously enhancing the coating's substantivity to flexible surfaces subjected to flexure, which properties thereby impart outstanding flake resistance and release value to said tape.

Those coating additives that reduce, control and/or eliminate crystal formation and enhance the substantivity of the coating to flexible surfaces when added to these coatings at modest levels include certain aliphatic, long chain, fatty alcohols having from between about 10 and 30 carbon atoms and/or various liquid surfactants such as polyethylene glycol sorbitan dialiphatic esters.

Suitable aliphatic, long chain, fatty alcohols for the crystal-free coatings of the present invention can be represented by the structural formula ROH, wherein R represents a long chain alkyl group having from 20 to 30 carbon atoms. Specific examples include:

| | | |
|---|---|---|
| 1-decanol | 1-heptadecanol | 1-pentacosanol |
| 1-undecanol | 1-octadecanol | 1-hexacosanol |
| 1-dodecanol | 1-nonadecanol | 1-heptacosanol |
| 1-tetradecanol | 1-eicosanol | 1-octacosanol |
| 1-pentadecanol | 1-heneicosanol | 1-nonacosanol |
| 1-hexadecanol | 1-tricosanol | 1-triacontanol |
| | 1-tetracosanol | |

Naturally occurring mixtures with substantial quantities of these fatty alcohols, or isomers thereof; including those chemically derived from natural sources also constitute suitable sources of aliphatic, long chain fatty alcohols for the purpose of this invention.

The long chain fatty alcohols can be represented by the structural formula ROH wherein R represents a long chain alkyl group having from 10 to 0.30 carbon atoms. These can be purchased commercially from Stepan, Proctor & Gamble and Aldrich Chemical Co. and a variety of companies processing vegetable and animal derived fatty alcohols.

Suitable liquid surfactants for the crystal-free coatings of the present invention include polyoxyethylene glycol sorbitan mono and di-aliphatic esters represented by the general formula:

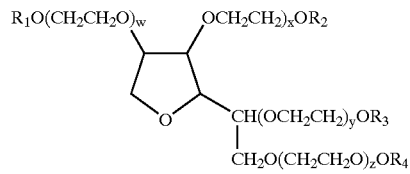

wherein $R_1$, $R_2$, $R_3$, $R_4$ are H or aliphatic acyl groups from (10 to 30) and the sum of w, x, y, and z is from between 20 and 80. These liquid surfactants are available under the trade names Emsorb®, Span®, Tween® from Cognis N.A. and ICI. Specific examples of these include:

PEG 20 sorbitan monooleate (Tween® 80, ICI);
PEG 40 sorbitan monostearate (Span 60®, ICI); and
PEG 40 sorbitan diisostearate (Emsorb® 2726, Cognis, N.A.).

Similar esterified, PEG-based surfactants, which are known to those having ordinary skilled in the art, are also suitable liquid surfactants.

One preferred embodiment of this invention thus comprises substantive coatings for flexible surfaces that, under flexure, resist cracking, flaking, breaking off, etc.

Another preferred embodiment of the present invention comprises a shred-resistant dental tape that physically removes biofilms from interproximal and subgingival sites.

Another preferred embodiment of the invention comprises a method of applying substantive coatings of biofilm disrupting substances to shred-resistant tapes which coatings are released onto and worked into biofilms during flossing.

A further preferred embodiment of the invention comprises shred-resistant tapes with substantive coatings that exhibit minimum flaking, yet achieve total release during flossing.

Yet another preferred embodiment of the invention comprises monofilament tapes with substantially crystal-free coatings that are substantive, saliva soluble and exhibit with a minimum of flaking.

Still another preferred embodiment of the invention comprises a shred-resistant dental tape with a substantive coating that helps physically remove biofilms when released from the tape during flossing.

A further preferred embodiment of the present invention comprises substantive coatings for dental tapes that contain biofilm disrupting and physically removing ingredients along with biologically active or chemotherapeutic ingredients, all of which are largely or totally released during flossing.

Still another preferred embodiment of the present invention comprises a method for treating interproximal and subgingival sites to remove subgingival and interproximal biofilms while treating said sites with active ingredients.

Yet another preferred embodiment of the invention comprises a method for manufacturing a shred-resistant dental tape that contains substantial levels of biofilm disrupting/removing ingredients that do not flake off; yet are totally releasable during flossing.

An other preferred embodiment of the invention comprises coated dental tapes with a flaking value of less than about 20.

A further preferred embodiment of the invention comprises a class of coated dental tapes with coating release values approaching about 100.

These and other embodiments of the invention are described in detail below.

DETAILED DESCRIPTION OF THE PREFERRED EMBODIMENTS

For the purposes of the present invention, "crystal-free" is defined as a smooth surface as distinguished from rough surface typical of crystalline coatings when observed through a 30× stereo zoom microscope.

For the purposes of the present invention, flaking resistance measures the propensity of the coatings of the present invention to flake off a flexible elastomeric, TEFLON®, bicomponent, or other polymeric dental tapes during flexure. Flaking resistance (or "flake value") is percentage value based on the reduction by weight of the crystal-free coating alter flexing, under suitably controlled and reproducible conditions, an 18-inch piece of the coated tape for 30 seconds.

For the purposes of the present invention, release value is measured after 18-inches of the tape is thoroughly flossed for 60 seconds. The percent of the crystal-free coating removed from the tape during flossing establishes the release value.

For the purposes of the present invention, dental tape is defined as monofilament tapes including elastomeric tapes such as Perident's FIBACLEAN® dental tape, PTFE tapes, such as Gore's GLIDE® dental tape, J&J's EASY SLIDE® dental tape and Colgate's TOTAL® dental tape and bicomponent tapes such as Oral-B's SATIN TAPE® dental tape.

Certain petroleum waxes are suitable and preferred additional additives for the crystal-free coating of the present invention. These include any of a range of relatively high molecular weight hydrocarbons (approximately $C_{16}$ to $C_{50}$), solid at room temperature, derived from the higher-boiling petroleum fractions. There are three basic categories of petroleum wax: paraffin (crystalline), microcrystalline, and petroleum. Paraffin waxes are produced from the lighter lube oil distillates, generally by chilling the oil and filtering the crystallized wax they have a melting point range between 48° C. (118° F.) and 71° C. (160° F.), Fully refined paraffin waxes are dry, hard, and capable of imparting good gloss. Microcrystalline waxes are produced from heavier lube distillates arid residue (one bottoms) usually by a combination of solvent dilution and chilling. They differ from paraffin waxes in having poorly defined crystalline structure, darker color, higher viscosity, and higher melting points—ranging from 63° C. (148° F.) to 93° C. (200° F.). The microcrystalline grades also vary much more widely than paraffins in their physical characteristics: some are ductile and others are brittle or crumble easily.

Petrolatum is derived from heavy residual lube stock by propane dilution and filtering or centrifuging. It is microcrystalline in character and semi-solid at room temperature. There are also heavier grades for industrial applications, such as corrosion preventives, carbon paper, and butcher's wrap. Traditionally, the terms slack wax, scale wax and refined wax were used to indicate limitations on oil content. Today, these classifications are less exact in their meanings, especially in the distinction between slack wax and scale wax. Natural waxes such as beeswax and carnauba wax are also suitable and may provide specifically desired properties.

Suitable additional ingredients in the crystal-free coating of the present invention include anti-plaque ingredients—such as MICRODENT® and ULTRAMULSION® as described in various U.S. patents to Hill, et al., including U.S. Pat. Nos. 4,911,927; 4,950,479; 5,032,387; 5,098,711; 5,165,913; 5,538,667; 5,561,959; 5,66,374 and 5,733,529. The foregoing are incorporated herein by reference.

Various other active ingredients can be included in the substantive saliva-soluble coatings applied to the various dental tapes of the present invention including antimicrobial, anti-tartar, whitening, cleaning, desensitizing, antibiotic, anti-inflammatory, anti-gingivitis ingredients, as well as prostaglandin ($PGE_2$) and C-reactive protein control substances.

Specific active ingredients suitable for use in the coated dental tape of the present invention include: fluoride, potassium nitrate, triclosan, chlorhexidine, cetylpyridinium chlorhexidine, domaphen bromide, metronidazole, doxycycline, aspirin, the essential oils in Listerine®, and mixtures thereof.

The substantial coatings for the dental tapes of the present invention can be further characterized as: (a) containing a crystal control substance, (b) being saliva soluble, (c) substantially crystal-free, and (d) comprising from between about 20% and 120% by weight of said tape, and having a flake value of less than about 20 and a release value of about 100.

Elastomeric dental tapes such as described in the referenced co-pending applications coated with the crystal-free coatings of the present invention are described in Table I below.

TABLE 1

| EXAMPLE | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| Ingredient | | | | | | | | | | | | | | | | | | |
| Ultramulsion 10-2.5 | 57.1 | 54.8 | 52.3 | 50.8 | 50.8 | 50.8 | 58.8 | 60.8 | | 60.1 | 55.1 | 51.1 | 60.1 | | 61.1 | 61.1 | 53.1 | 57.1 |
| POLOXAMER 407 | | | | | | | | | 60.1 | | | | | 60.1 | | | | |
| Emsorb 2726 | 12.5 | 7.5 | 12.5 | 9 | 5 | 3 | 3 | 0 | 3 | 3 | 3 | 3 | 3 | 3 | 4 | 3 | 3 | 3 |
| Stearyl Alcohol | 9.2 | 10.5 | 8 | 7 | 11 | 13 | 15 | 16 | 15 | 15 | 15 | 15 | 15 | 15 | 10 | 8 | 15 | 15 |
| Insoluble Saccharin | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 |
| Propyl gallate | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Spicemint Flavor | 4 | 4 | 4 | 4 | 4 | 4 | 4 | 4 | 5 | 5 | 5 | 5 | 5 | 5 | 5 | 5 | 5 | 5 |
| Vanilla Mint Flavor | 4 | 4 | 4 | 4 | 4 | 4 | 4 | 4 | 5 | 5 | 5 | 5 | 5 | 5 | 5 | 5 | 5 | 5 |
| tetrasodiumpyrophosphate | 8 | 14 | 14 | 10 | 10 | 10 | 10 | 10 | 10 | | 10 | 14 | 4 | | 6 | 6 | 10 | 6 |
| Dicalcium phosphate | | | | | | | | | | 10 | | | 6 | 10 | | | | |
| Microcrystalline Wax ML 445 | | | 10 | 10 | 10 | 0 | 0 | 0 | 0 | 5 | 5 | | 0 | 7 | 10 | 7 | 7 | |
| Triclosan | 3.3 | 3.3 | 3.3 | 3.3 | 3.3 | 3.3 | 3.3 | 3.3 | | | | | | | | | | |

TABLE 1-continued

| EXAMPLE | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| Observation | | | | | | | | | | | | | | | | | | |
| Need heat to wind | y | | | n | y | y | n | y | Y | y | y | y | y | y | y | y | y | y |
| Bobbin tack (1 = poor, 5 = good) | 1 | | 5 | 5 | 3 | 4 | | 4 | 3 | 2 | 4 | 4 | 3 | 3 | 4 | 3 | 4 | 4 |
| Flake resistance | | | | | | | | | | | | | | | | | | |
| Feels sticky (1 = no, 5 = very) | | | | 5 | 4 | 4 | 2 | 1 | 2 | 2 | 3 | 3 | 3 | 1 | 4 | 3 | 4 | 4 |
| Load of two samples | 29/19 | Na | Na | 43/50 | 28/11 | 53/39 | 58/43 | 33/20 | 51/40 | 33 | 46/53 | 40/39 | 38/38 | 50/37 | 48 | 45 | 38/39 | 43/39 |
| Release Value | 98 | 97 | 100 | 96 | 100 | 99 | 100 | 100 | 96 | 99 | 98 | 100 | 97 | 99 | 100 | 96 | 100 | 100 |

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A substantive coating for monofilament dental tape comprising:
    at least one crystal control substance; and
    an effective amount of at least one biologically active ingredient, wherein the coating is saliva-soluble and comprises between about 20% and about 120% by weight of the tape and has a flake value of less than about 20 and a release value of about 90 to 100.

2. The substantive coating for monofilament dental tape of claim 1, wherein the crystal control substance is selected from the group consisting of long chain fatty alcohols or mixtures thereof and liquid surfactants having the standard formula:

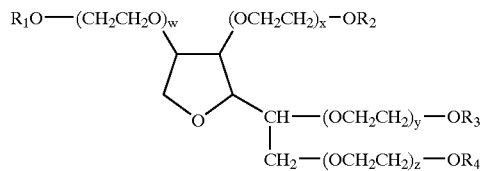

wherein $R_1$ to $R_4$ represent H or aliphatic acyl groups having from 10 to 30 carbon atoms.

3. The substantive coating for monofilament dental tape of claim 2, wherein the sum of w, x, y, and z is from between about 20 and about 80.

4. The substantive coating for monofilament dental tape of claim 2, wherein the long chain fatty alcohol has the standard formula:

R—OH wherein R represents a long chain alkyl group having from 10 to 30 carbon atoms.

5. The substantive coating for monofilament dental tape of claim 2, wherein the long chain fatty alcohol is selected from the group consisting of 1-tetradecanol, 1-eicosanol, 1-octacosanol, 1-pentadecanol, 1-heneicosanol, 1-nonacosanol, 1-hexadecanol, 1-tricosanol, 1-triacontanol, and 1-tetracosanol.

6. The substantive coating for monofilament dental tape of claim 2, wherein the long chain fatty alcohol is present in its natural isomeric form.

7. The substantive coating for monofilament dental tape of claim 1, wherein the crystal control substance comprises an esterified, polyethylene glycol (PEG-) based surfactant.

8. The substantive coating for monofilament dental tape of claim 1, wherein the crystal control substance is a polyethylene glycol sorbitan dialiphatic ester.

9. The substantive coating for monofilament dental tape of claim 1, wherein the at least one biologically active ingredient is selected from the group consisting of antimicrobial, anti-tartar, anti-plaque, whitening, cleaning, desensitizing, antibiotic, anti-inflammatory, anti-gingivitis ingredients, prostaglandin ($PGE_2$), and C-reactive protein control substances.

10. The substantive coating for monofilament dental tape of claim 9, wherein the antimicrobial substance is selected from the group consisting of chlorhexidine, cetylpyridinium chloride, domaphen bromide, triclosan, metronidazole, and mixtures thereof.

11. The substantive coating for monofilament dental tape of claim 1, further comprising a wax.

12. The substantive coating for monofilament dental tape of claim 11, wherein the wax is selected from the group consisting of paraffin waxes, microcrystalline waxes, petroleum waxes, and natural waxes.

13. The substantive coating for monofilament dental tape of claim 11, wherein the wax is substantially solid at room temperature and comprises a $C_{16}$ to $C_{50}$ hydrocarbon.

14. The substantive coating for monofilament dental tape of claim 1, further comprising a sweetening agent.

15. The substantive coating for monofilament dental tape of claim 14, wherein the sweetener comprises saccharin.

16. The substantive coating for monofilament dental tape of claim 1, further comprising a flavoring agent.

17. The substantive coating for monofilament dental tape of claim 16, wherein the flavoring agent is spicemint flavored or vanilla mint flavored.

18. The substantive coating for monofilament dental tape of claim 1, further comprising an abrasive agent.

19. Monofilament dental tape coated with a substantive coating, the coating comprising:
    at least one crystal control substance; and
    an effective amount of at least one biologically active ingredient, wherein the coating is saliva-soluble and comprises between about 20% and about 120% by weight of the tape and has a flake value of less than about 20 and a release value of about 90 to 100.

20. The coated monofilament dental tape of claim 19, wherein the monofilament dental tape is shred-resistant.

21. The coated monofilament dental tape of claim 19, wherein the crystal control substance is selected from the group consisting of long chain fatty alcohols or mixtures thereof and liquid surfactants having the standard formula:

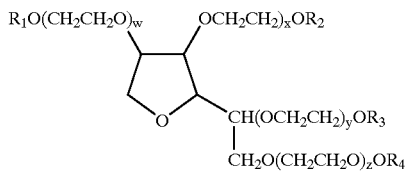

wherein $R_1$ to $R_4$ represent H or aliphatic acyl groups having from 10 to 30 carbon atoms and the sum of w, x, y, and z is from between about 20 and about 80.

22. The coated monofilament dental tape of claim 19, wherein the long chain fatty alcohol has the standard formula:

R—OH wherein R represents a long chain alkyl group having from 10 to 30 carbon atom.

23. The coated monofilament dental tape of claim 19, wherein the at least one biologically active ingredient is selected from the group consisting of antimicrobial, antitartar, anti-plaque, whitening, cleaning, desensitizing, antibiotic, anti-inflammatory, anti-gingivitis ingredients, prostaglandin ($PGE_2$), and C-reactive protein control substances.

24. The coated monofilament dental tape of claim 23, wherein the antimicrobial substance is selected from the group consisting of chlorhexidine, cetylpyridinium chloride, domaphen bromide, triclosan, metronidazole, and mixtures thereof.

25. The coated monofilament dental tape of claim 19, wherein the coating further comprises a wax selected from the group consisting of paraffin waxes, microcrystalline waxes, petroleum waxes, and natural waxes.

26. The coated monofilament dental tape of claim 19, further comprising a sweetening agent.

27. The coated monofilament dental tape of claim 19, further comprising a flavoring agent.

28. The coated monofilament dental tape of claim 19, further comprising an abrasive agent.

29. The coated monofilament dental tape of claim 19, wherein the coating exhibits minimum cracking, fracturing, and flaking when physically removing biofilms from interproximal and subgingival surfaces.

30. The coated monofilament dental tape of claim 19, wherein the at least one biologically active ingredient is releasable upon working into and physically removing biofilms from interproximal and subgingival spaces.

31. The costed monofilament dental tape of claim 19, wherein the coating is substantially crystal-free.

32. A method of manufacturing a coated monofilament dental tape having a substantive coating comprising at least one crystal control substance and an effective amount of at least one biologically active ingredient, wherein the coating is saliva-soluble and comprises between about 20% and about 120% by weight of the tape and has a flake value of less than about 20 and a release value of about 90 to 100, the method comprising the steps of:

a. introducing the tape to a loading means containing the coating which is fluid and maintained substantially uniform, while being held at a temperature above the melting temperature of the coating;

b. removing excess coating from the tape by doctoring or calendering the excess coating off the coated tape after coating, and c. cooling the coated tape and winding the same onto master spools prior to bobbin winding.

* * * * *